United States Patent [19]

Madison et al.

[11] Patent Number: 5,478,357
[45] Date of Patent: Dec. 26, 1995

[54] ACTIVATION OF BLEACH PRECURSORS WITH IMINE QUATERNARY SALTS

[75] Inventors: Stephen A. Madison, New City, N.Y.; Janet L. Coope, Cliffside Park, N.J.

[73] Assignee: Lever Brothers Company, Division of Conopco, Inc., New York, N.Y.

[21] Appl. No.: 278,775

[22] Filed: Jul. 21, 1994

Related U.S. Application Data

[62] Division of Ser. No. 152,040, Nov. 12, 1993, Pat. No. 5,360,569.

[51] Int. Cl.$^6$ .......................................... D06L 3/02
[52] U.S. Cl. ...................... 8/111; 252/102; 252/99; 252/174; 252/174.12; 252/186.42; 252/186.43; 252/186.44; 252/524; 546/150
[58] Field of Search ..................... 8/111; 252/99, 252/102, 174, 174.12, 186.42, 186.43, 186.44, 524; 546/150

[56] References Cited

U.S. PATENT DOCUMENTS

| | | |
|---|---|---|
| 3,976,652 | 8/1976 | Kupchan et al. . |
| 4,192,877 | 3/1980 | Savarese et al. . |
| 4,194,987 | 3/1980 | Brubakcer . |
| 4,362,639 | 12/1982 | Euoga ........................................ 252/99 |
| 4,668,688 | 5/1987 | Bernath et al. . |
| 4,678,792 | 7/1987 | Nickl et al. . |
| 4,997,590 | 3/1991 | Bowling .............................. 252/186.31 |
| 5,041,232 | 8/1991 | Batal et al. . |
| 5,045,223 | 9/1991 | Batal et al. . |
| 5,047,163 | 9/1991 | Batal et al. . |
| 5,059,608 | 10/1991 | Takasugi et al. . |

OTHER PUBLICATIONS

Hanquet, Lusinchi & Milliet, Tetrahedron vol. 49, No. 2, pp. 423–428, (1993) (month unknown).
Hanquet, Lusinchi, Tet. Let., vol. 34, No. 33, pp. 5299–5302 (1993) (month unknown).
Hanquet, Lusinchi & Milliet, Tet. Let. vol. 29, No. 32, pp. 3941–3944 (1988) (month unknown).
Hanquet, Lusinchi & Milliet, Tet. Let. No. 29, No. 23, pp. 2817–2818, (1988) (month unknown).
Hanqut, Lusinchi & Milliet, C. R. Acad. Sci. Paris, pp. 625–628, (1991) (month unknown).

*Primary Examiner*—Prince Willis, Jr.
*Assistant Examiner*—Alan D. Diamond
*Attorney, Agent, or Firm*—Milton L. Honig

[57] ABSTRACT

A bleaching composition is described that includes a peroxygen compound such as sodium perborate, an oxygen transfer agent in the form of a quaternary imine salt and a bleach precursor. The quaternary imine salt at relatively low concentrations enhances the activity of the precursor. A method for bleaching substrates is also provided, especially a method for cleaning fabrics.

11 Claims, No Drawings

ACTIVATION OF BLEACH PRECURSORS WITH IMINE QUATERNARY SALTS

This is a Divisional application of Ser. No. 08/152,040 filed Nov. 12, 1993 now U.S. Pat. No. 5,360,569.

BACKGROUND OF THE INVENTION

1. Field of the Invention

The invention relates to a new type of low temperature bleaching system and a method of cleaning substrates therewith.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this technology is found in certain fabric bleaching detergent powders incorporating tetraacetylethylenediamine (TAED) and sodium nonanoyloxybenzene sulfonate (SNOBS).

TAED is effective only under warm-hot wash conditions, i.e. above 30° C. Although this material is widely employed in Europe with laundry detergent, cold water consumer washing habits have not permitted use in the United States. SNOBS can operate at lower temperatures than TAED. For this reason, it has been commercialized in the United States but its performance could still be improved.

Another problem with carboxylic acid ester precursors such as TAED and SNOBS is that conversion to peracid is inefficient. A further difficulty is that they are not catalytic. Once the ester has been perhydrolyzed, it can no longer be recycled. Accordingly, relatively large amounts of precursor are necessary. Amounts as high as 8% may be necessary in a detergent formulation for bleaching fabrics. At such high use levels, cost for these relatively expensive chemicals is of major concern.

Recently there has been reported in U.S. Pat. Nos. 5,047,163 5,045,233 and 5,041,232, all to Batal and Madison, a system for activating bleach precursors based upon sulfonimines and N-sulfonyloxaziridines. While these compounds have been shown to be highly effective, even better catalysts are sought, especially for wash temperatures around 10° C., such as are experienced in Japan.

Outside the context of consumer products, there have been reports of catalytic oxidizing agents. Hanquet and coworkers, in a series of articles, reported preparation of a new class of stable olefin epoxidizing agents, namely oxaziridinium salts. See Hanquet, Lusinchi and Milliet, Tet. Let. (1988) 3941; Hanquet, Lusinchi and Milliet, C. R. Acad. Sci. Paris (1991) Series II, 625; and Hanquet, Lusinchi and Milliet, Tet. Let. (1988) 2817. These oxaziridinium salts were prepared by peracid or monopersulfate oxidation of a corresponding quaternary imine salt under alkaline conditions. Epoxides were reported to be formed from the reaction of olefins with the oxaziridinium salts. Reactions were conducted either in organic solvents or in organic solvent-water biphasic media. Beyond use as a synthetic tool, there is no suggestion of any possible application for quaternary imine salt chemistry to the problem of removing stains in consumer applications, such as in cleaning fabrics.

It is an object of the present invention to provide an improved bleaching system and detergent composition containing such system that operates over a wide temperature range including that of under 30° C.

It is another object of the present invention to improve the performance of bleach precursors that normally would be inoperative under low temperature wash conditions.

A further object of the present invention is to provide bleach improvement through catalysts effective in relatively small amounts so as to avoid any substantial incremental costs.

A still further object of the present invention is to provide a method for bleaching stained substrates such as clothes, household hard surfaces including sinks, toilets and the like, and even dentures.

Other objects of the present invention will become more readily apparent through the following summary, detailed description and examples.

SUMMARY OF THE INVENTION

A bleaching composition is provided comprising:

(i) from about 1 to about 60% by weight of a peroxygen compound;

(ii) from about 0.01 to about 10% of an oxygen transfer agent whose structure is:

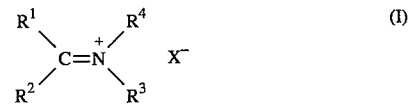

wherein:

$R^1$ and $R^4$ may be a substituted or unsubstituted radical selected from the group consisting of hydrogen, phenyl, aryl, hetercyclic ring, alkyl and cycloalkyl radicals:

$R^2$ may be a substituted or unsubstituted radical selected from the group consisting of hydrogen, phenyl, aryl, hetercyclic ring, alkyl, cycloalkyl, nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a radical selected from the group consisting of cycloalkyl, polycyclo, heterocyclic and aromatic ring systems;

$X^-$ is a counterion stable in the presence of oxidizing agents; and (iii) from about 0.1 to about 40% of a bleach precursor that reacts with peroxide anion and forms therewith a percarboxylic acid, percarbonic acid or perimidic acid.

Additionally, there is provided a method for bleaching a stained substrate comprising treating the stained substrate with a peroxygen compound, an oxygen transfer agent whose structure is $R^1R^2C=N^+R^3R^4X^-$ with radical groups as defined above, and a bleach precursor.

DETAILED DESCRIPTION

Now it has been found that relatively small amounts of quaternary imine salts can boost the performance of bleach precursor-peroxygen compound systems. Increased bleaching effectiveness has been noted on consumer and industrial articles whose stains can be removed even at relatively low temperatures. Thus, quaternary imine salt chemistry is more than a synthetic curiosity as in the conversion of olefins to epoxides reported by Hanquet et al. Unlike the Hanquet et al biphasic system that requires an organic solvent, quaternary imine salts can be devised for use in completely aqueous wash systems.

Quaternary imine salts covered by the present invention are those whose structure is:

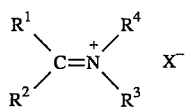

(I)

wherein:

$R^1$ and $R^4$ may be hydrogen or a $C_1-C_{30}$ substituted or unsubstituted radical selected from the group consisting of phenyl, aryl, heterocyclic ring, alkyl and cycloalkyl radicals:

$R^2$ may be hydrogen or a $C_1-C_{30}$ substituted or unsubstituted radical selected from the group consisting of phenyl, aryl, heterocyclic ring, alkyl, cycloalkyl, nitro, halo, cyano, alkoxy, keto, carboxylic and carboalkoxy radicals;

$R^3$ may be a $C_1-C_{30}$ substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a cycloalkyl, polycyclo, heterocyclic or aromatic ring systems.

$X^-$ is a counterion stable in the presence of oxidizing agents.

Heterocyclic rings according to this invention include cycloaliphatic and cycloaromatic type radicals incorporating an oxygen, sulfur and/or nitrogen atom within the ring system. Representative nitrogen heterocycles include pyridine, pyrrole, imidazole, triazole, tetrazole, morpholine, pyrrolidine, piperidine and piperazine. Suitable oxygen heterocycles include furan, tetrahydrofuran and dioxane. Sulfur heterocycles may include thiophene and tetrahydrothiophene.

Counterion $X^-$ may be selected from chloride, bromide, sulfate, methosulfate, sulfonate, p-toluenesulfonate, borontetrafluoride, $PF_5^-$, phosphate and cyano radicals.

The term "substituted" is defined in relation to $R^1$, $R^2$, $R^3$ and $R^4$ as a substituent which is a nitro, halo, cyano, $C_1-C_{20}$ alkyl, amino, aminoalkyl, thioalkyl, sulfoalkyl, carboxyester, hydroxy, $C_1-C_{20}$ alkoxy, polyalkoxy or $C_1-C_{40}$ quaternary di- or trialkylammonium function.

The most preferred quaternary imine salts are the 3,4-dihydroisoquinolinium salts of structure II where $R^5$ and $R^6$ are defined by the same radicals as that for $R^2$:

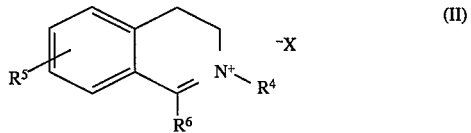

(II)

Table I lists specific illustrative compounds represented by structure II.

TABLE I

| COMPOUND | $R^4$ | $R^5$ | $R^6$ | $X^-$ |
|---|---|---|---|---|
| 1 | CH₃ | H | H | BF₄⁻ |
| 2 | CH₃ | H | H | P-tosylate⁻ |
| 3 | CH₃ | CH₃ | H | Cl⁻ |
| 4 | CH₃ | NO₂ | H | Br⁻ |
| 5 | CH₃ | Cl | H | BF4⁻ |
| 6 | CH₃ | OCH₃ | H | brosylate⁻ |
| 7 | phenyl | H | H | CH₃SO₄⁻ |
| 8 | benzyl | phenyl | H | Cl⁻ |
| 9 | (CH₂)₂OH | CN | H | PF₆⁻ |
| 10 | CH₃ | CH₂COCH₃ | H | PF₆⁻ |
| 11 | (CH₃)₂CH | COCH₃ | H | CH₂CH₃SO₄⁻ |
| 12 | CH₃ | SO₂⁻Na⁺ | H | Cl⁻ |
| 13 | CH₃(CH₂)₁₁ | H | H | p-tosylate⁻ |
| 14 | CH₃(CH₂)₁₅ | Br | H | CH₃SO₄⁻ |
| 15 | CH₂CH₂N(CH₂)₃ | H | H | Cl⁻ |
| 16 | CH₃ | F | H | Cl⁻ |
| 17 | CH₃ | CF₃ | H | PF₆⁻ |
| 18 | CH₃ | CH₂OPO₃Na₂ | H | Cl⁻ |
| 19 | CH₃ | pyridyl | H | Cl⁻ |
| 20 | 2-pyridyl | H | H | Cl⁻ |
| 21 | CH₃ | CH₂N⁺(CH₃)₃ | H | CH₃SO₄⁻ |
| 22 | CH₃CH₂O(CH₂)₂ | H | H | CH₃SO₄⁻ |
| 23 | CH₃ | (CH₂)₇CH₃ | H | Cl⁻ |
| 24 | CH₃ | CO₂⁻Na⁺ | H | Cl⁻ |
| 25 | (CH₂)₇CH₃ | H | H | p-tosylate⁻ |
| 26 | CH₃ | H | CH₃ | Cl⁻ |
| 27 | CH₃ | H | phenyl | Cl⁻ |

Additional compounds according to the present invention are outlined below as structures III through X.

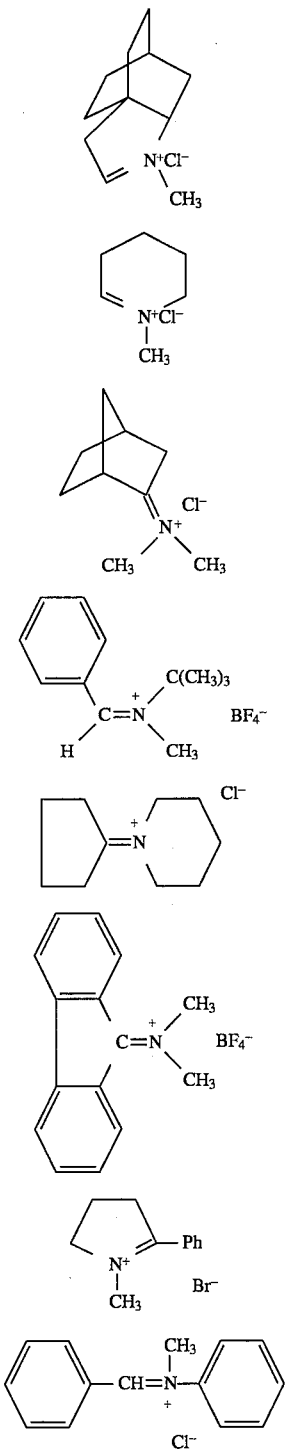

The foregoing oxygen transfer agents may be incorporated into detergent bleach compositions along with a further essential component which is a peroxygen compound capable of yielding peroxide anion in an aqueous solution.

Amounts of oxygen transfer agent suitable for the present invention may range from about 0.01 to 10%, preferably from about 0.2 to 5%, optimally from about 0.5 to 1.5% by weight of the composition.

The peroxygen compound may be present from about 1 to 60%, preferably from about 1.5 to 25%, optimally from about 2 to 10% by weight.

The molar ratio of peroxide anion (or a peroxygen compound generating the equivalent amount of peroxide anion) to oxygen transfer agent will range from about 1500:1 to about 1:2, preferably from about 150:1 to 1:1, optimally from about 60:1 to 3:1.

Amounts of bleach precursor relative to oxygen transfer agent will be present in the molar ratio from about 250:1 to about 1:20, preferably from about 100:1 to about 1:1, optimally between about 25:1 to 2:1.

Peroxide anion sources are well-known in the art. They include the alkalimetal peroxides, organic peroxides such as urea peroxide, and inorganic persalts, such as the alkalimetal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkyl hydroperoxides are another suitable class of peroxygen compounds. Examples of these materials include cumene hydroperoxide and t-butyl hydroperoxide.

Organic peroxyacids may also be suitable as the peroxygen compound. Such materials have a general formula:

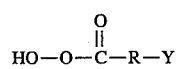

wherein R is an alkylene or substituted alkylene group containing from 1 to about 22 carbon atoms or a phenylene or substituted phenylene group, and Y is hydrogen, halogen, alkyl, aryl or

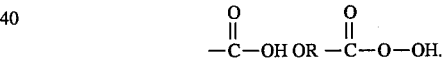

The organic peroxyacids usable in the present invention can contain either one or two peroxy groups and can be either aliphatic or aromatic. When the organic peroxyacid is aliphatic, the unsubstituted acid has the general formula:

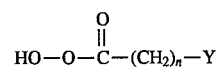

where Y can be, for example, H, $CH_3$, $CH_2Cl$, COOH, or COOOH; and n is an integer from 1 to 20.

When the organic peroxy acid is aromatic, the unsubstituted acid has the general formula:

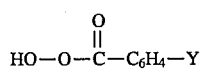

wherein Y is hydrogen, alkyl, haloalkyl, halogen or COOH or COOOH.

Typical monoperoxy acids useful herein include alkyl peroxyacids and aryl peroxyacids such as:

(i) peroxybenzoic acid and ring-substituted peroxybenzoic acid, e.g. peroxy-α-naphthoic acid;

(ii) aliphatic, substituted aliphatic and arylalkyl monoperoxy acids, e.g. peroxylauric acid, peroxystearic acid, and N,N-phthaloylaminoperoxycaproic acid (PAP); and (iii) amidoperoxyacids, e.g. mononoylamide of either peroxysuccinic acid (NAPSA) or of peroxyadipic acid (NAPAA).

Typical diperoxy acids useful herein include alkyl diperoxyacids and aryldiperoxy acids, such as:

(iii) 1,12-diperoxydodecanedioic acid;

(iv) 1,9-diperoxyazelaic acid;

(v) diperoxybrassylic acid: diperoxysebacic acid and diperoxyisophthalic acid;

(vi) 2-decyldiperoxybutane-1,4-dioic acid;

(vii) 4,4'-sulfonylbisperoxybenzoic acid;

(viii) N,N'-terephthaloyl-di(6-aminoperoxycaproic acid) (TPCAP).

Particularly preferred organic acids are peracetic acid, monoperoxyphthalic acid (magnesium salt hexahydrate), PAP, TPCAP and diperoxydodecanedioic acid. Under certain circumstances, hydrogen peroxide itself may directly be employed as the peroxygen compound.

A third critical element in the compositions of this invention is a bleach precursor that reacts with peroxide anion and forms therewith a peracid, percarbonic acid or perimidic acid. Precursors of this invention are water-soluble materials, being soluble generally to an extent of at least 1%, preferably at least about 5% by weight at 25° C. and pH 7. Certain precursors of this invention may be further defined by the Per-Acid Formation Test wherein the precursor will have a titre of at least 1.5 ml of 0.1 N sodium thiosulphate. This test may be found in U.S. Pat. No. 3,177,148 (Bright et al) herein incorporated by reference.

Precursors which may be utilized for purposes of the present invention include:

(a) Diacylated and polyacylated amines, such as N,N,N', N'-tetraacetylmethylenediamine, N,N,N',N'-tetracetylethylenediamine, N,N-diacetylaniline and N,N-diacetyl-p-toluidine; 1,3-diacylated hydantoins such as, for example, 1,3-diacetyl-5,5-dimethyl hydantoin and 1,3-dipropionyl hydantoin; acetoxy-N,N,N'-polyacylmalonamide, for example, acetoxy-(N,N')-diacetylmalonamide;

(b) N-alkyl-N-sulphonyl carbonamides, for example, the compounds N-methyl-N-mesylbenzamide, N-methyl-N-mesyl-p-nitrobenzamide, and N-methyl-N-mesyl-p-methoxybenzamide;

(c) N-acylated cyclic hydrazides, acylated triazones or urazoles, for example monoacetylmaleic acid hydrazide;

(d) O,N,N-trisubstituted hydroxylamines, such as O-benzoyl-N,N-succinyl hydroxylamine, O-p-methoxybenzoyl-N,N-succinylhydroxylamine, O-p-nitrobenzoyl-N,N-succinylhydroxylamine and O,N,N-triacetyl hydroxylamine;

(e) N,N'-diacyl-sulfurylamides, for example, N,N'-dimethyl-N,N'-diacetylsulfurylamide and N,N'-diethyl-N,N'-dipropionyl sulfurylamide;

(f) Triacylcyanurates, for example, triacetyl cyanurate and tribenzoyl cyanurate;

(g) Carboxylic acid anhydrides, such as benzoic anhydride, m-chlorobenzoic anhydride, phthalic anhydride and 4-chloro phthalic anhydride;

(h) Esters, for example, sodium acetyloxybenzene sulfonate, sodium nonanoyloxybenzene sulfonate and sodium benzoyloxybenzenesulfonate; and $C_2$–$C_{20}$ fatty acyl monoesters of hexoses and pentoses, for example, glucose pentaacetate, xylose tetraacetate, 1-benzoyl-2, 3,4,6-tetraacetylglucose and 1-octanoyl-2,3,4,6-tetraacetylglucose;

(i) 1,3-Diacyl-4,5-diacyloxy-imidazolidine, for example, 1,3-diformyl-4,5-diacetoxy-imidazolidine 1,3-diacetyl-4,5-diacetoxy-imidazolidine and 1,3-diacetyl-4,5-dipropionyloxy-imidazoline;

(j) Tetraacetylglycoluril and tetrapropionylglycoluril;

(k) Diacylated 2,5-diketopiperazine such as 1,4-diacetyl-2,5-diketopiperazine, 1,4-dipropionyl-2,5-diketopiperazine and 1,4-dipropionyl-3,6-dimethyl2,5-diketopiperazine;

(l) Acylation products of propylenediurea or 2,2-dimethylpropylenediurea (2,4,6,8-tetraaza-bicyclo-(3,3,1)-nonane-3,7-dione or its 9,9-dimethyl derivative), especially the tetraacetyl- or the tetrapropionylpropylenediurea or their dimethyl derivatives;

(m) Carbonic acid esters, for example, the sodium salts of p-(ethoxycarbonyloxy)-benzenesulfonic acid and p-(propoxycarbonyloxy)benzenesulphonic acid;

(n) Acyloxy-(N,N')polyacyl malonamides, such as α-acetoxy-N,N'-diacetyl malonamide; and (o) Quaternary ammonium substituted peroxycarbonic or carboxylic acid esters such as 2-(N,N,N-trimethylammonio) ethyl 4-sulfophenyl carbonate.

The precursors mentioned under (a), (h) and (j) are of special interest, particularly N,N,N',N'-tetraacetylethylenediamine (TAED), tetraacetylglycoluril (TAGU), glucose pentaacetate, xylose tetraacetate, sodium acetyloxybenzene sulfonate (SABS) and sodium nonanoyloxybenzene sulfonate(SNOBS).

Bleach systems of the present invention may be employed for a wide variety of purposes, but are especially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, such as soap or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 1% to about 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide reaction products; the reaction products of fatty acids such as coconut fatty acids esterified with isethionic acid and neutralized with sodium hydroxide: sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefinic sulfonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulfonates; sodium ($C_{16}$–$C_{18}$) alkyl sulfates and sodium ($C_{16}$–$C_{18}$) alkyl ether sulfates.

Examples of suitable nonionic surface-active compounds which may be used preferably together with the anionic surface-active compounds, include in particular, the reaction products of alkylene oxides, usually ethylene oxide, with alkyl ($C_6$–$C_{22}$) phenols, generally 2–25 EO, i.e. 2–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylenediamine. Other so-called nonionic surface-actives include alkylpolyglycosides, polyhydroxy fatty acid amides (e.g. $C_{12}$–$C_{18}$ N-methyl glucamide), long chain tertiary amine oxides, long chain tertiary phosphine oxides and dialkyl sulfoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5 and about 25% by weight, with lower amounts of about 0.5 to about 5% being generally sufficient for lather control. Amounts of soap between about 2 and about 20%, especially between about 5 and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials; (2) precipitating materials; (3) calcium ion-exchange materials; and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di-succinates, oxydisuccinate, crystalline or amorphous aluminosilicates and mixtures thereof.

Polycarboxylic homo- and copolymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxygen compound should range in amount to yield anywhere from about 0.05 to about 250 ppm active oxygen per liter of water, preferably between about 1 to 50 ppm. Within the wash media, the amount of oxygen transfer agent initially present should be from about 0.01 to about 300 ppm, preferably from about 1 to 100 ppm. Bleach precursor may be present in the wash media in an amount from about 0.05 to 500 ppm, preferably from about 5 to 200 ppm. Surfactant optionally may be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, antiredeposition agents such as sodium carboxymethylcellulose and alkyl or substituted alkylcellulose ethers, other stabilizers such as ethylenediaminetetraacetic acid, fabric softening agents, inorganic salts such as sodium sulfate and usually present in very small amounts, fluorescent whitening agents, perfumes, enzymes such as proteases, cellulases, lipases and amylases, germicides and colorants.

Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in nonaqueous liquids such as liquid nonionic detergents.

The following examples will more fully illustrate the embodiments of this invention. All pads, percentages and proportions referred to herein and in the appended claims are by weight unless otherwise illustrated.

EXAMPLE 1

3,4-Dihydroisoquinoline

The title compound was prepared using the procedure of Yamazaki, *Chem. Lett.* (1992) 823. The starting reagent 1,2,3,4-tetrahydroisoquinoline was distilled under vacuum at 85° C. (~10 mmHg) prior to use.

Into a 3-necked 12L Morton flask equipped with a mechanical stirrer were placed 1,2,3,4-tetrahydroisoquinoline (66.6 grams, 0.5 mol) and 2 liters of methylene chloride. A solution of potassium persulfate (189.23 grams, 0.7 mol), sodium hydroxide (48 grams, 1.2 mol) and water (4.4 L) was added. While the solution was vigorously mixed, a 0.05M aqueous solution of nickel sulfate hexahydrate (200 mL, 0.01 mol) was added to the biphasic mixture. Fine black precipitates deposited immediately, and the resulting mixture was stirred vigorously at room temperature. The reaction temperature became slightly elevated to about 35° C. After 3.5 hours of stirring, the black color changed to a light brown colored solution. The mixture was filtered through a short Celite frit column to remove any insoluble materials. The organic layer in the filtrate was separated by extraction with methylene chloride. The organic layer was dried over magnesium sulfate and concentrated down to give 56 g (85% yield) of a dark red liquid. Distillation at 105° C. under vacuum (~11 mmHg) provided 46 g (70%) of a yellow liquid.

The sample contained two impurities: 4% of isoquinoline and 1% of unreacted 1,2,3,4-tetrahydroisoquinoline.

$^1$H NMR (CDCl$_3$/TMS):$\delta$2.73 (t,2H) 3.77 (t,2H), 7.09–7.37 (m,4H), 8.33 (s, 1H). The isoquinoline is shown at $\delta$3.10 (t,2H), 4.01 (s,2H), 7.59–7.94 (m,4H), 8.51 (d,2H) and 9.25 (s, 1H).

N-Methyl-3,4-dihydroisoquinolinium p-toluenesulfonate (Imine Quat OTs)

The title compound was prepared using the procedure described by Koelsch et al in *J. Am. Chem. Soc.*(1953) 75, 2095. In a 250-mL one-necked round-bottomed flask equipped with a magnetic stir bar and a reflux condenser were placed 3,4-dihydroisoquinoline (8.27 grams, 63 mmol) and 40 ml of methanol. The mixture was stirred and cooled to 0° C. A solution of methyl p-toluenesulfonate (11.73 g, 63 mmol) and 70 ml of methanol was added dropwise. The color of the solution remained clear and yellow. The mixture was heated to reflux for 6 hours. The methanol was then removed in vacuo to provide a quantitative yield (20 g) of an off-white solid (mp 115°–119° C.). The solid was pulverized and washed with 40 ml of acetone at room temperature. Suction filtration provided a white solid in 88% yield: mp 124°–127° C.

$^1$H NMR (D$_2$O):$\delta$2.27 (s,3H), 3.15 (t,2H), 3.73 (S,3H), 3.93 (t,2H), 7.18–7.78 (m,8H), 8.77 (s,1H). Impurities observed at 4.46 (s), 8.0–8.3 (m), 9.4 (s) were due to N-methylisoquinolinium p-toluenesulfonate.

EXAMPLE 2

N-Methyl-3,4-dihydroisoquinolinium borontetrafluoride (Imine Quat BF$_4$)

The title compound was prepared according to the literature procedure (Hanquet, G., Lusinchi, X., Milliet, P., *Tetrahedron Letters*, (1988), 29, 3941).

In a 50 ml 2-necked round-bottomed flask equipped with a reflux condenser and stir bar under nitrogen were placed of 3,4-dihydroisoquinoline (1.0 g, 7.6 mmol) and 30 ml of anhydrous toluene. Once in solution, trimethyloxonium tetrafluoroborate (1.12 g, 7.6 mmol) was added, which was not soluble in toluene. The reaction mixture was stirred at room temperature for 10 hours. The reaction mixture was separated into two levels. The dark-red brown viscous liquid was decanted out and dried in an oven to remove any excess toluene.

$^1$H NMR (DMSO/TMS): $\delta$3.23 (2H,m), 3.73 (3H,s), 4.02 (2H,s), 7.47–7.82 (4H,m) and 9.18 (1H,s).

EXAMPLE 3

Stain bleaching experiments were conducted in a Terg-O-Tometer in 500 ml of milli-Q water using two tea-stained cotton cloths measuring 3×4 inches. In a typical test, 0.75 g of commercial detergent was added to the system and the pH of the solution was constantly buffered to the indicated level by the addition of dilute aqueous sodium hydroxide or hydrochloric acid. A given oxidant was added to the system followed by an appropriate amount of quaternary imine salt. Washes were carded out at the indicated temperature for 15 minutes.

Stain bleaching was measured reflectometrically using a Colorgard System/05 Reflectometer. $\Delta$R is the reflectance difference between washed and unwashed cloths; effects due to detergent are not subtracted. Bleaching was indicated by an increase in reflectance, reported as $\Delta\Delta$R. In general a $\Delta\Delta$R of one unit is perceivable in a paired comparison while $\Delta\Delta$R of two units is perceivable monadically.

Table II and III report the bleaching activity of the N-methyl-3,4-dihydroisoquinolinium borontetrafluoride (BF$_4$) and p-toluenesulfonate (OTs) salts.

TABLE II

| | | | Tea Stain (BC-1) at pH 9.5 and 32° C. | | | |
|---|---|---|---|---|---|---|
| BASE* | PEROXIDE‡ | SALT COUNTERION | IMINE QUAT SALT CONCENTRATE | $\Delta$R PEROXIDE | $\Delta$R IMINE QUAT SALT & PEROXIDE | $\Delta\Delta$R IMINE QUAT SALT |
| P-SURF ® | TAED/PB | BF$_4$ | $6.0 \times 10^{-5}$M | 2.48 | 10.98 | 8.50 |
| ULTRA SURF ® | TAED/PB | OTs | $6.0 \times 10^{-5}$M | 1.59 | 11.69 | 10.10 |
| ULTRA ALL ® | TAED/PB | BF$_4$ | $6.0 \times 10^{-6}$M | 2.08 | 3.14 | 1.06 |

*P-Surf ®: anionic/nonionic/phosphate builder: dosage 1.5 g/l.
Ultra-Surf ®: 15% anionic/8% nonionic/30% zeolite/20% carbonate; dosage 1.02–1.1 g/l.
Ultra-All ®: 14% anionic/38% carbonate/29% sulfate; dosage 1.02–1.1 g/l.
‡Denotes 7.5 ppm active oxygen peracetic acid from TAED and 25 ppm active oxygen sodium perborate.

TABLE III

Tea Stain (BC-1) at pH 10 and 18° C.

| BASE* | PEROXIDE | SALT COUNTERION | IMINE QUAT SALT CONCENTRATE | ΔR PEROXIDE | ΔR IMINE QUAT SALT & PEROXIDE | ΔΔR IMINE QUAT SALT |
|---|---|---|---|---|---|---|
| P-SURF® | TAED/PB[1] | BF$_4$ | $6.0 \times 10^{-5}$M | 1.51 | 12.10 | 10.59 |
| ULTRA SURF® | TAED/PB[1] | BF$_4$ | $6.0 \times 10^{-5}$M | 0.96 | 11.26 | 10.30 |
| ULTRA SURF® | TAED/PB[1] | OTs | $6.0 \times 10^{-5}$M | 0.95 | 13.20 | 12.25 |
| ULTRA SURF® | TAED/PB[2] | BF$_4$ | $6.0 \times 10^{-5}$M | 0.75 | 8.23 | 7.48 |

[1]Denotes 10 ppm active oxygen peracetic acid from TAED and 32 ppm active oxygen Sodium Perborate.
[2]Denotes 7.5 ppm active oxygen peracetic acid from TAED and 25 ppm active oxygen Sodium Perborate.

EXAMPLE 4

This Example details the effect against stain other than that of tea. Table IV establishes that the quat imine salt enhances the bleaching performance of TAED against wine stains.

TABLE IV

Wine Stain (EMPA-114) at pH 9.5 and 32° C.

| BASE | PEROXIDE | SALT COUNTERION | IMINE QUAT SALT CONCENTRATE | ΔR PEROXIDE | ΔR IMINE QUAT SALT & PEROXIDE | ΔΔR IMINE QUAT SALT |
|---|---|---|---|---|---|---|
| ULTRA SURF® | TAED/PB | OTs | $6.0 \times 10^{-5}$M | 18.1 | 20.1 | 2.00 |
| ULTRA SURF® | TAED/PB | OTs | $2.0 \times 10^{-5}$M | 17.5 | 19.4 | 1.90 |
| ULTRA SURF® | TAED/PB | OTs | $6.0 \times 10^{-6}$M | 17.9 | 17.7 | −0.20 |

‡Denotes 7.5 ppm active oxygen peracetic acid from TAED and 25 ppm active oxygen sodium perborate.

The results set forth in Tables IV show that the bleaching action of a typical precursor system such as TAED and perborate is improved by the presence of N-methyl-3,4-dihydroisoquinolinium salts.

The foregoing description and Examples illustrate selected embodiments of the present invention. In light thereof, various modifications will be suggested to one skilled in the art, all of which are within the spirit and purview of this invention.

What is claimed is:

1. A method for bleaching a stained substrate, said method comprising contacting said stained substrate in an aqueous medium with a peroxygen compound, a bleach precursor and with an oxygen transfer agent whose structure is:

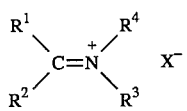

(I)

wherein:

R$^1$ and R$^4$ are substituted or unsubstituted radicals independently selected from the group consisting of hydrogen, phenyl, aryl, heterocyclic ring, alkyl and cycloalkyl radicals;

R$^2$ is a substituted or unsubstituted radical selected from the group consisting of hydrogen, phenyl, aryl, heterocyclic ring, alkyl, cycloalkyl, nitro, halo, cyano, alkoxy, keto, carboxylic and carboalkoxy radicals;

R$^3$ is a substituted or unsubstituted radical selected from the group consisting of phenyl, aryl, heterocyclic ring, alkyl, cycloalkyl, nitro, halo, and cyano radicals;

or R$^1$ with R$^2$ and R$^2$ with R$^3$ respectively together form a radical selected from the group consisting of cycloalkyl, polycyclo, heterocyclic and aromatic ring systems;

X$^-$ is a counterion stable in the presence of oxidizing agents; and said peroxygen compound to oxygen transfer agent being present in a molar ratio ranging from 150:1 to about 1:2, and said bleach precursor to oxygen transfer agent being present in a molar ratio ranging from about 250:1 to about 1:20.

2. A method according to claim 1 wherein the ratio of peroxygen compound to oxygen transfer agent ranges from about 60:1 to 1:1.

3. A method according to claim 1 wherein said substrate is a denture.

4. A method according to claim 1 wherein the ratio of bleach precursor to oxygen transfer agent ranges from about 100:1 to about 1:1.

5. A method according to claim 1 wherein the ratio of peroxygen compound to oxygen transfer agent ranges from about 60:1 to about 3:1 and the ratio of bleach precursor to oxygen transfer agent ranges from about 25:1 to about 2:1.

6. A method according to claim 1 wherein said substrate is a fabric.

7. A method according to claim 1 wherein said substrate is selected from the group consisting of dishes, glassware and tableware.

8. A method according to claim 1 wherein the oxygen transfer agent is a 3,4-dihydroisoquinolinium salt.

9. A method for bleaching a stained substrate, said method comprising contacting said stained substrate in an aqueous medium with a peroxygen compound, a bleach precursor and with an oxygen transfer agent whose structure is:

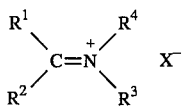

wherein:

$R^1$ and $R^4$ are substituted or unsubstituted radicals independently selected from the group consisting of hydrogen, phenyl, aryl, hetercyclic ring, alkyl and cycloalkyl radicals;

$R^2$ is a substituted or unsubstituted radical selected from the group consisting of hydrogen, phenyl, aryl, heterocyclic ring, alkyl, cycloalkyl, nitro, halo, cyano, alkoxy, keto, carboxylic and carboalkoxy radicals;

$R^3$ is a substituted or unsubstituted radical selected from the group consisting of phenyl, aryl, heterocyclic ring, alkyl, cycloalkyl, nitro, halo, and cyano radicals;

or $R^1$ with $R^2$ and $R^2$ with $R^3$ respectively together form a radical selected from the group consisting of cycloalkyl, polycyclo, heterocyclic and aromatic ring systems;

$X^-$ is a counterion stable in the presence of oxidizing agents; and said contacting occurring in said medium containing about 0.05 to about 250 ppm per liter of medium of active oxygen from the peroxygen compound, about 0.05 to about 500 ppm per liter of medium of bleach precursor and about 0.01 to about 300 ppm per liter of medium of oxygen transfer agent, said peroxygen compound to oxygen transfer agent being present in a molar ratio ranging from 150:1 to about 1:2.

10. A method according to claim 9 wherein the oxygen transfer agent is a 3,4-dihydroisoquinolinium salt.

11. A method according to claim 9 wherein the ratio of peroxygen compound to oxygen transfer agent ranges from about 60:1 to 1:1.

* * * * *